United States Patent [19]

Inoue

[11] Patent Number: 5,084,158

[45] Date of Patent: Jan. 28, 1992

[54] FLOW CELL FOR ELECTROLYTE MEASURING DEVICE

[75] Inventor: Shoichi Inoue, Hino, Japan

[73] Assignee: Olympus Optical Co., Ltd., Tokyo, Japan

[21] Appl. No.: 573,907

[22] Filed: Aug. 27, 1990

[30] Foreign Application Priority Data

Aug. 31, 1989 [JP] Japan ................... 1-102168

[51] Int. Cl.⁵ .............................................. G01N 27/26
[52] U.S. Cl. .................................. 204/411; 204/409; 204/416
[58] Field of Search ............... 204/409, 411, 412, 415, 204/416, 418, 153.1

[56] References Cited

U.S. PATENT DOCUMENTS

| | | | |
|---|---|---|---|
| 4,596,649 | 6/1986 | Hofmeier et al. | 204/409 X |
| 4,627,893 | 12/1986 | Cormier et al. | 204/411 X |
| 4,640,821 | 2/1987 | Mody et al. | 204/409 X |
| 4,797,191 | 1/1989 | Metzner et al. | 204/411 X |
| 4,871,439 | 10/1989 | Enzer et al. | 204/411 X |
| 4,889,611 | 12/1989 | Blough, Jr. | 204/411 |

Primary Examiner—Nam X. Nguyen
Attorney, Agent, or Firm—Frishauf, Holtz, Goodman & Woodward

[57] ABSTRACT

A flow cell comprises an examining liquid flow passage, a comparison liquid flow passage communicated with the examining liquid flow passage, plural ion selective electrode openings communicated with the examining liquid flow passage, and a comparison electrode opening communicated with the comparison liquid flow passage. The examining liquid flow passage is provided with linear inlet and outlet parts which are communicated at their one ends with each of the ion selective electrode openings, and curved parts each of which connects the linear outlet part which is communicated with the ion selective electrode opening to the linear inlet part which is communicated with the next ion selective electrode opening.

10 Claims, 3 Drawing Sheets

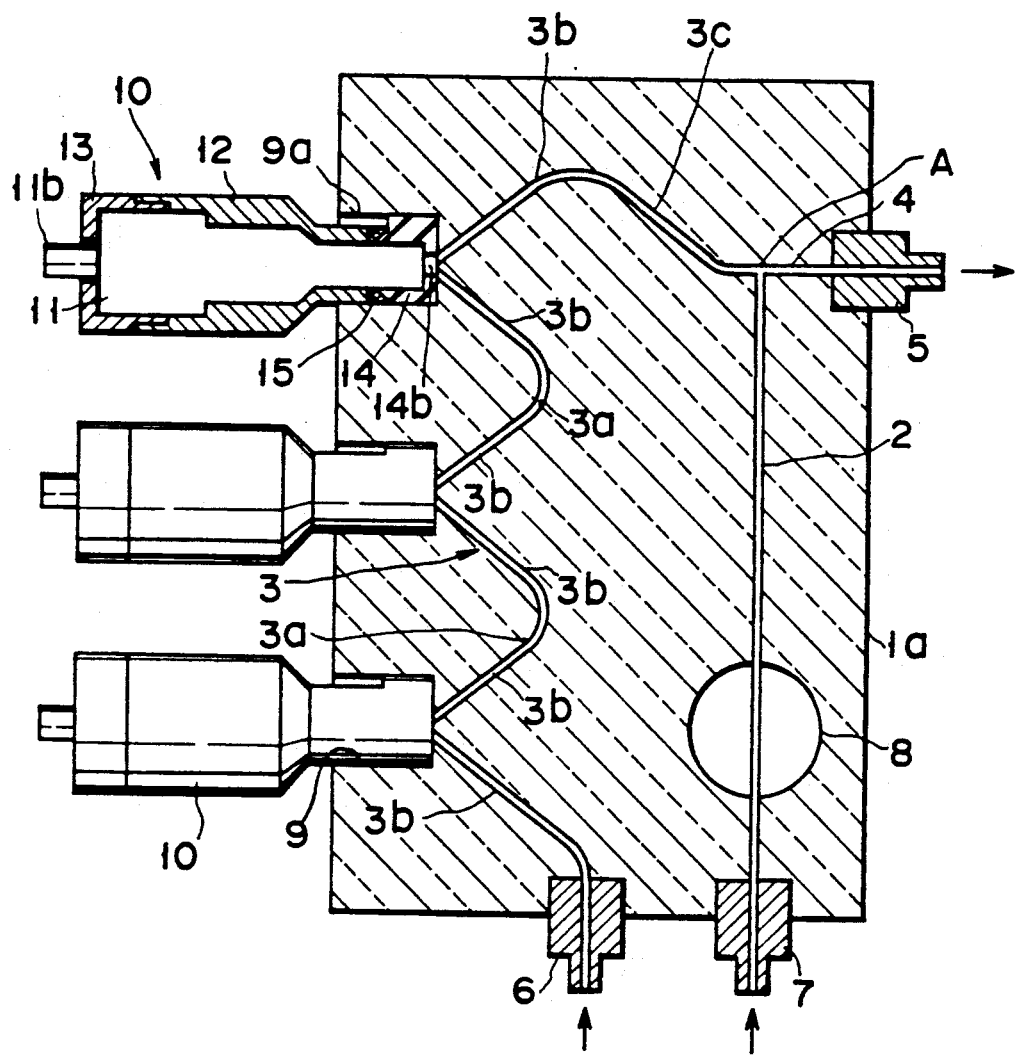
F I G. 1

FLOW CELL FOR ELECTROLYTE MEASURING DEVICE

BACKGROUND OF THE INVENTION

1. Field of the Invention

The present invention relates to a flow cell for a device measuring densities of electrolytes in blood serum, blood plasma, urin and the like.

2. Description of the Related Art

In a case where densities of electrolytes in liquids to be examined are continuously measured by the automatic chemical analytic device, the "flow system" for measuring them while pouring the liquids one after another is employed because the system is simple in mechanical arrangement and the system enables the liquids to be easily treated.

Japanese Patent Disclosure Sho 60-222760 having a title "Measuring Device Provided With Ion Selective Electrodes" discloses a device comprising a member (or flow cell) for defining a measuring passage provided with an inlet and outlet through which liquids are injected and discharged, and ion selective electrodes arranged along the measuring passage at a certain interval, wherein said measuring passage has plural curved parts and each of the curved parts is located adjacent to one of the electrodes.

The conventional measuring device has one measuring passage and one comparison liquid flow passage through which liquids flow to a reference electrode. In a case where the speed of measuring electrolytes in liquids is made high, plural flow cells, plural reference electrodes and means for keeping the temperature of each of the plural flow cells certain are needed. In addition, each of the plural flow cells need one reference electrode and one temperature adjuster means. This causes values obtained by measuring electrolytes in liquids to become different every flow cell.

SUMMARY OF THE INVENTION

The object of the present invention is therefore to provide an electrolyte measuring device or flow cell capable of carrying out the electrolyte measurement at higher speed without finding any irregularity in values measured.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a partly-sectioned view showing a fundamental arrangement of the present invention;

DETAILED DESCRIPTION OF THE PREFERRED EMBODIMENTS

A fundamental arrangement of one embodiment according to the present invention will be described with reference to FIGS. 1 through 4.

Figure 2:
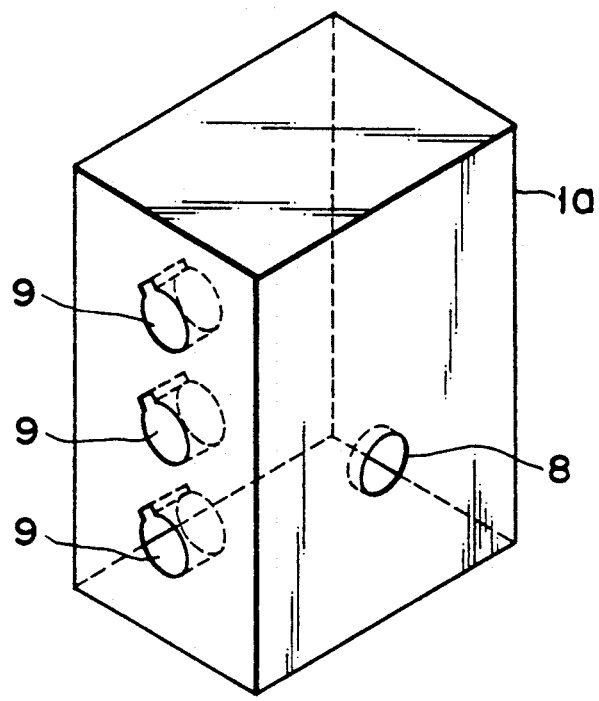
FIG. 2 is a perspective view showing a part of the arrangement in FIG. 1.

In FIG. 1, reference numeral 1a denotes a transparent hard flow cell made of epoxy resin and shaped like a rectangular parallelepiped, as shown in FIG. 2. A linear comparison liquid flow passage 2 and a zigzag examining or measuring liquid flow passage 3 are formed in the flow cell 1a. The examining liquid flow passage 3 comprises linear parts 3b and curved parts 3a in which the adjacent linear parts 3b are connected at their one ends by the curved part 3a. The adjacent linear parts 3b of the examining liquid flow passage 3 are cut off by a sensitive film face 11a of an ion selective electrode which will be described later. In other words, the adjacent linear parts 3b are opposed at their other ends to the sensitive film face 11a of the ion selective electrode. The comparison liquid flow passage 2 and the examining liquid flow passage 3 have circular sections substantially same in diameter and they are communicated with each other at their junction (A). A linear part 3c of the examining liquid flow passage 3 which is communicated with the junction (A) is tilted upward from the junction (A) to the linear part 3b of the passage 3 not to allow comparison liquid injected into the comparison liquid flow passage 2 to flow back into the examining liquid flow passage 3 because of osmotic pressure. The linear part 3c of the examining liquid flow passage 3 is communicated with a flow-out passage 4 and an outlet connector 5 which is screwed into the flow cell 1a.

The other end of the examining liquid flow passage 3 is communicated with an inlet connector 6 which is also screwed into the flow cell 1a.

The comparison liquid flow passage 2 is communicated at one end thereof with the junction (A) and at the other end thereof with an inlet connector 7 which is screwed into the flow cell 1a. Reference numeral 8 represents an opening or recess which is provided with a female screw thread and into which a well-known comparison electrode is screwed in such a way that the sensitive film face at the front end of the comparison electrode is contacted with the comparison liquid flow passage 2.

Three openings or recesses 9 are arranged in a vertical line on one side of the flow cell 1a with a certain interval interposed between them. Each of them has a female screw thread and it is shaped like a circle and communicated at its inner face with one end of the linear part 3b of the examining liquid flow passage 3.

An ion selective electrode 10 is intended to measure electrolytes such as Na, K and Cl and the matter of which the sensitive film of the electrode is made changes depending upon the kind of electrolytes to be measured, but the structural arrangement of the electrode is left same.

In the case of the electrode 10, an electrode body 11 is arranged in a pair of hollow holders 12 and 13 which are screwed each other.

The holder 12 has a male screw thread on its front end and it is screwed into the opening 9 in the flow cell 1a.

Figure 4:
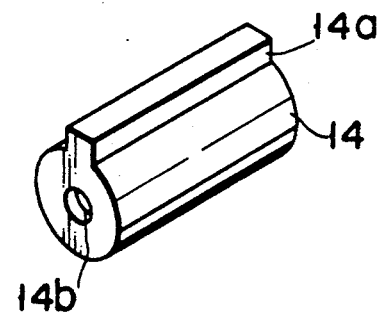
FIG. 4 is a perspective view showing a part of the arrangement in FIG. 1.

As shown in FIG. 4, a packing 14 is shaped like a cylinder and provided with a projection 14a on the top thereof, which is fitted into a groove 9a extending on the inner circumferential face of the circular opening 9 along the axial direction thereof, so that the packing 14 can be held in the opening 9 not to rotate therein. The packing 14 has a circular hole 14b in the center of its closed front end and this circular hole 14b is communicated with the end face of the linear part 3b of the passage 3.

A ring-shaped washer 15 is interposed between the packing 14 and the front of the holder 12 and when the holder 12 is screwed into the opening 9, the washer 15 pushes the packing 14 in the direction in which the holder 12 is screwed so as to fix the front of the electrode body 11.

Figure 3:
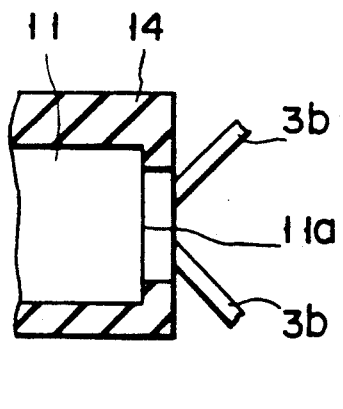
FIG. 3 is a view showing a part of the arrangement in FIG. 1 enlarged.

As shown in FIG. 3, the sensitive film face 11a of the electrode body 11 is opposed to the circular hole 14b of the packing 14 and thus opposed to the end faces of the linear parts 3b of the passage 3.

The rear holder 13 is intended to prevent the electrode body 11 from getting out of the front holder 12 and it is screwed into the holder 12.

Reference numeral 11b denotes an electric connection terminal extending from the rear end of the electrode body 11 and a lead line for connecting the electrode body 11 to a well-known voltmeter (not shown) is attached to the terminal.

When a liquid to be examined is injected into the examining liquid flow passage 3 through the connector 6, the liquid flows through the first linear part 3b of the passage 3 and contacts the sensitive film face 11a of the electrode 10 located lower than the other two electrodes 10. It further flows through the second, third and fourth parts 3b, 3a and 3b of the passage 3 and contacts the sensitive film face 11a of the electrode 10 located between the other two electrodes 10. It further flows through the fifth, sixth and seventh parts 3b, 3a and 3b of the passage 3 and contacts the sensitive film face 11a of the electrode 10 located higher than the other two electrodes 10. It further flows through the eighth and ninth parts 3b and 3c of the passage 3 and contacts a liquid to be compared, and then discharged through the connector 5.

As shown in FIG. 3, each of the sensitive film faces 11a of the electrodes 10 is positioned relative to the linear parts 3b of the passage 3 in such a way that the liquid to be examined is blown to the sensitive film face 11a through the end face of one linear part 3b and taken into the end face of the other linear part 3b.

This enables the ion electrodes 10 to more quickly respond to the liquid to be examined.

The comparison liquid is injected into the comparison liquid flow passage 2 through the connector 7 and contacted with the sensitive film face of the comparison electrode and then with the examining liquid at the junction (A) while flowing through the passage 2, and finally discharged through the connector 5.

When the liquid to be examined is successively contacted with the ion selective electrodes 10 as described above, electrolytes in the liquid can be quantitatively obtained on the basis of the comparison liquid by measuring potentials of the ion selective electrodes 10 generated. The temperature of the flow cell is kept certain by a temperature adjuster (not shown).

Another embodiment of the flow cell according to the present invention will be described with reference to FIG. 5. Same components as those shown in FIGS. 1 through 4 will be denoted by same reference numerals and description on these components will be omitted.

A second examining or measuring liquid flow passage 15 comprises curved parts 15a and linear parts 15b and 15c and it is as seen in the case of the examining liquid flow passage 3 shown in FIG. 1 how the passage 15 is formed by these parts 15a, 15b and 15c.

Connectors 16 and 17 correspond to those 6 and 5 shown in FIG. 1 and a junction (B) to the one (A) shown in FIG. 1.

A flow cell 1b corresponds to the one 1a shown in FIGS. 1 and 2.

A comparison liquid flow passage 2 is formed in the flow cell 1b and two lines of examining liquid flow passages 3 and 15 are formed in the flow cell 1b. A comparison electrode is screwed into the opening 8.

The ion selective electrodes 10 are electrically connected to the comparison electrode at the junction (B).

Same or different liquids to be examined are alternately or simultaneously injected into the two lines of the examining liquid flow passages 3 and 15 through the connectors 6 and 16, and both of the liquids are contacted with each other at the junction (B) while carrying out the electrolyte measurement.

When two lines of the examining liquid flow passages are formed in one flow cell in this manner, the electrolyte measurement can be attained at a higher speed. In addition, the flow cell 1b needs only one temperature adjuster, so that values obtained by the measurement can be found certain.

A further embodiment of the flow cell according to the present invention will be described with reference to FIG. 6.

Figure 6:
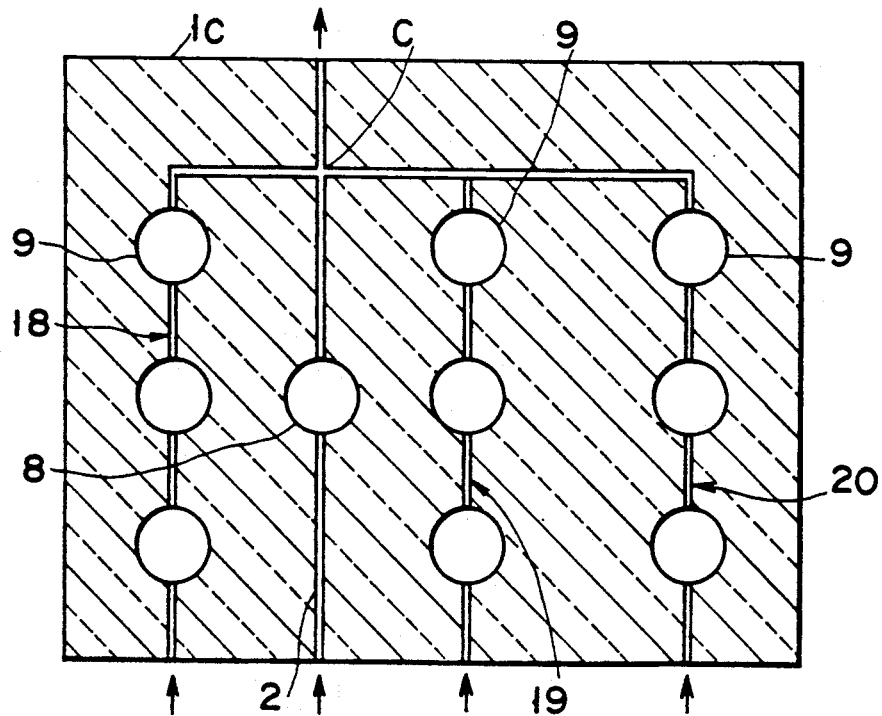
FIG. 6 is a diagram intended to explain another embodiment of the flow cell according to the present invention.

FIG. 6 is a diagram showing three lines of the examining liquid flow passages and one line of the comparison liquid flow passage formed in a flow cell. Same components as those shown in FIG. 1 will be denoted by same reference numerals and description on these components will be omitted.

Figure 5:
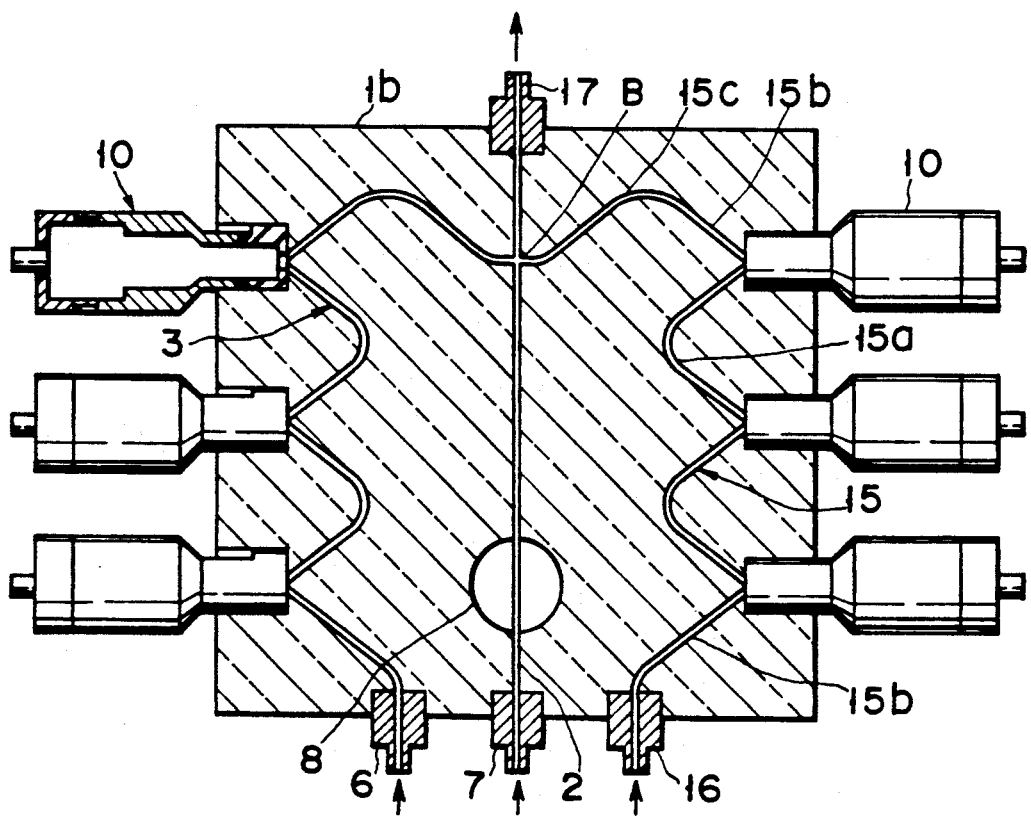
FIG. 5 is a partly-sectioned view showing an embodiment of the flow cell according to the present invention.

Same examining liquid flow passages 18, 19 and 20 as those 3 and 15 shown in FIGS. 1 and 5, and a comparison liquid flow passage 2 are formed in a flow cell 1c. Symbol (C) represents a junction.

It should be understood that the present invention is not limited to the above-described examples. The matter of which the flow cell is made may be metal, synthetic resin or glass. Further, four or more lines of the examining liquid flow passages may be formed in a flow cell.

According to the present invention, the speed of measuring electrolytes in a liquid to be examined can be made higher. In addition, the irregularity of values measured using plural flow cells can be reduced.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A flow cell comprising:
   a body which includes at least two measuring liquid flow passages;
   a comparison liquid flow passage in said body, and inlet and outlet ports coupled to said comparison liquid flow passage;
   a plurality ion selective electrode openings communicated with said measuring liquid flow passages;
   each of said measuring liquid flow passages having linear inlet and outlet parts, said linear inlet and outlet parts being communicated at one end thereof with respective ion selective electrode openings;
   each of said measuring liquid flow passages being coupled to inlet and outlet ports;
   means for connecting other ends of said linear outlet parts, which are communicated with the respective ion selective electrode openings, to the other end of the linear inlet part which is communicated with the next successive ion selective electrode opening; and
   junction means for connecting the outlet ports of said measuring liquid flow passages to the outlet port of said comparison liquid flow passage.

2. The flow cell according to claim 1, wherein said body has one side on which said inlet ports of said measuring liquid flow passages are provided.

3. The flow cell according to claim 2, wherein said comparison liquid flow passage is positioned between said measuring liquid flow passages.

4. The flow cell according to claim 3, comprising two of said measuring liquid flow passages; and wherein said two measuring liquid flow passages are positioned in said body so that they are symmetrical with respect to said comparison liquid flow passage.

5. The flow cell according to claim 1, wherein each of said connecting means comprises a curved part connected to said other ends of said linear outlet and inlet parts of said measuring liquid flow passage.

6. The flow cell according to claim 1, comprising only a single comparison liquid flow passage coupled to said at least two measuring liquid flow passages.

7. The flow cell according to claim 6, wherein said comparison liquid flow passage is positioned between said measuring liquid flow passages.

8. The flow cell according to claim 6, comprising two of said measuring liquid flow passages; and wherein said two measuring liquid flow passage are positioned in said body so that they are symmetrical with respect to said comparison liquid flow passage.

9. The flow cell according to claim 6, wherein each of said connecting means comprises a curved part connected to said other ends of said linear outlet and inlet parts of said measuring liquid flow passage.

10. The flow cell according to claim 1, wherein said ion selective electrode openings each comprise a sensitive film face.

* * * * *

UNITED STATES PATENT AND TRADEMARK OFFICE
CERTIFICATE OF CORRECTION

PATENT NO. : 5,084,158
DATED : January 28, 1992
INVENTOR(S) : INOUE et al

It is certified that error appears in the above-identified patent and that said Letters Patent is hereby corrected as shown below:

Title Page -

Section [56] References Cited, under "Foreign Patent Document", insert the following:

--60-222760    11/1985    Japan--.

Signed and Sealed this

Thirty-first Day of August, 1993

Attest:

BRUCE LEHMAN

Attesting Officer

Commissioner of Patents and Trademarks